United States Patent [19]

Stanislowski et al.

[11] Patent Number: 4,511,490
[45] Date of Patent: Apr. 16, 1985

[54] COOPERATIVE ENZYMES COMPRISING ALKALINE OR MIXTURES OF ALKALINE AND NEUTRAL PROTEASES WITHOUT STABILIZERS

[75] Inventors: Anna G. Stanislowski, Tracy; Richard J. Wiersema, Pleasanton, both of Calif.

[73] Assignee: The Clorox Company, Oakland, Calif.

[21] Appl. No.: 508,449

[22] Filed: Jun. 27, 1983

[51] Int. Cl.³ .............. C11D 7/42; C11D 3/386; D06M 16/00
[52] U.S. Cl. .............. 252/174.12; 252/DIG. 12; 435/42; 435/219; 435/220; 435/221; 435/222; 435/264
[58] Field of Search .............. 435/42, 264, 219, 220, 435/221, 222; 252/174.12, DIG. 12

[56] References Cited

U.S. PATENT DOCUMENTS

| | | | |
|---|---|---|---|
| 3,451,935 | 6/1969 | Roald et al. | 252/135 |
| 3,506,582 | 4/1970 | Gertzman | 252/157 |
| 3,513,071 | 5/1970 | Fehmerling | 195/2 |
| 3,519,570 | 7/1970 | McCarty | 252/135 |
| 3,532,599 | 10/1970 | Cooperman | 195/3 |
| 3,574,120 | 4/1971 | Siebert et al. | 252/132 |
| 3,600,318 | 8/1971 | Mass | 252/99 |
| 3,627,688 | 12/1971 | McCarty et al. | 252/153 |
| 3,661,786 | 5/1972 | Desforges | 252/99 |
| 3,676,374 | 7/1972 | Zaki et al. | 252/551 |
| 3,682,842 | 8/1972 | Innerfield | 252/539 |
| 3,717,550 | 2/1973 | Ziffer | 195/63 |
| 3,761,420 | 9/1973 | Bogardus | 252/171 |
| 3,776,693 | 12/1973 | Smith et al. | 8/142 |
| 3,781,212 | 12/1973 | Smillie | 252/89 |
| 3,813,342 | 5/1974 | Cooperman | 252/170 |
| 3,819,528 | 6/1974 | Berry | 252/153 |
| 3,985,686 | 10/1976 | Barrat | 252/547 |
| 4,016,040 | 4/1977 | Win et al. | 195/68 |
| 4,067,773 | 1/1978 | Martin | 195/63 |
| 4,087,368 | 5/1978 | Borrello | 252/89 R |
| 4,090,973 | 5/1978 | Maguire et al. | 252/174 |
| 4,092,175 | 5/1978 | Martin | 134/42 |
| 4,101,457 | 7/1978 | Place et al. | 252/559 |
| 4,115,292 | 9/1978 | Richardson et al. | 252/90 |
| 4,115,308 | 9/1978 | Guerry | 252/135 |
| 4,136,045 | 1/1979 | Gault et al. | 252/135 |
| 4,142,999 | 3/1979 | Bloching et al. | 252/544 |
| 4,162,987 | 7/1979 | Maquire, Jr. et al. | 252/135 |
| 4,238,345 | 12/1980 | Guilbert | 252/174.12 |
| 4,242,219 | 12/1980 | Bogerman et al. | 252/174.12 |
| 4,243,543 | 1/1981 | Guilbert et al. | 252/105 |
| 4,243,546 | 1/1981 | Shaer | 252/174.12 |
| 4,261,868 | 4/1981 | Hora et al. | 252/529 |
| 4,272,396 | 6/1981 | Fukano et al. | 252/174.12 |
| 4,285,738 | 8/1981 | Ogata | 134/26 |
| 4,287,082 | 9/1981 | Tolfo et al. | 252/174.12 |
| 4,287,101 | 9/1981 | Nishio et al. | 252/537 |
| 4,305,837 | 12/1981 | Kaminsky et al. | 252/174.12 |
| 4,318,818 | 3/1982 | Letton et al. | 252/174.12 |

FOREIGN PATENT DOCUMENTS

| | | |
|---|---|---|
| 1000628 | 11/1976 | Canada . |
| 1112534 | 11/1981 | Canada . |
| 0066323 | 12/1982 | European Pat. Off. . |
| 2919622 | 11/1980 | Fed. Rep. of Germany . |
| 57-145197 | 3/1981 | Japan . |
| 57-145198 | 3/1981 | Japan . |
| 57-155299 | 3/1981 | Japan . |
| 889689 | 9/1979 | Sweden . |
| 1463422 | 2/1977 | United Kingdom . |
| 2021142 | 11/1979 | United Kingdom . |
| 2037804 | 7/1980 | United Kingdom . |
| 2041968 | 9/1980 | United Kingdom . |
| 1582200 | 12/1980 | United Kingdom . |
| 2101167 | 1/1983 | United Kingdom . |

OTHER PUBLICATIONS

P. N. Christensen et al., "Proteolytic Enzymes in Non Built Liquid Detergents," *J. Amer. Oil Chemist's Soc.*, Jan. 1973, vol. 55, pp. 109–113.

W. G. Allen et al., "Amylases and Their Properties," *The Baker's Digest*, Jun. 1974, pp. 14–22, 57.

J. Hollo, "Mechanism of Amylolytic Starch Degradation," *Die Staerke*, 25. Jahrgang, Nr. 1, Seite 1–12, 1973.

Ottesen et al., "Subtilisin: Stability Properties and Secondary Binding Sites," in: *Structure–Function Relationships of Proteolytic Enzymes*, (1970), pp. 175–186.

Smith et al., "Some Structure–Function Relationships in the Subtilisins," in: *Structure–Function Relationships of Proteolytic Enzymes*, (1970), pp. 161–171.

Matsubara and Feder, "Other Bacterial, Mold, and Yeast Proteases," in: Boyer, *The Enzymes*, vol. III, pp. 721–795.

Primary Examiner—John E. Kittle
Assistant Examiner—Mukund J. Shah
Attorney, Agent, or Firm—Joel J. Hayashida; Stephen M. Westbrook

[57] ABSTRACT

A stable, cooperative enzyme system which is stable under use conditions is disclosed which comprises at least two enzymes having activity towards a relatively complex substrate with at least partial activity over the same pH range, wherein their combined activities are greater than the sum of their individual activities as determined by the formula:

$$\left[ \frac{\text{Actual Activities } (E_1 + E_2) - \text{Expected Activities } (E_1 + E_2)}{\text{Expected Activities } (E_1 + E_2)} \right] \times 100\%$$

wherein $E_1$ and $E_2$ are said enzymes.

No additional chemical stabilizers, modifiers or activators are added to the enzymes of this invention.

Particularly preferred enzymes in this invention are proteases having optimal activity in acidic, neutral or alkaline media, and mixtures of the same.

A method of making this cooperative enzyme system is also disclosed.

The enzyme systems of this invention have a wide variety of uses in cleaning and other applications.

33 Claims, No Drawings

COOPERATIVE ENZYMES COMPRISING ALKALINE OR MIXTURES OF ALKALINE AND NEUTRAL PROTEASES WITHOUT STABILIZERS

BACKGROUND OF THE INVENTION

Enzymes have been used for numerous industrial, commercial and research purposes. In the laundry detergent field, however, they have only recently been included in various synthetic detergent mixtures, whether in dry, solid phase, or in liquid phase. Approximately twenty years ago, proteolytic enzymes (also referred to in this description as "proteases" or "proteinases") were first proposed for use in various detergent compositions, but since that time, virtually hundreds of patents and other references have been published, disclosing formulas of varying cleaning effectiveness. Illustrative of such detergent/enzyme mixtures is Zaki et al, U.S. Pat. No. 3,676,374, which discloses and claims an enzyme/detergent composition having a mixture of 2-35% anionic, and 2-30% nonionic surfactants, and 0.001-5.0% proteolytic enzyme.

Starting from about 1971, various cleaning compositions, whether laundry detergents, dishwashing detergents, dry cleaning chemicals, etc. were patented in which two or more *different* subclasses of enzymes, typically, proteases and amylases, were included in the formulas thus patented. Included among these patents are: Letton et al, U.S. Pat. No. 4,318,818; Maguire Jr., et al, U.S. Pat. No. 4,162,987; Kaminsky et al, U.S. Pat. No. 4,305,837; Richardson et al, U.S. Pat. No. 4,115,292; Place et al, U.S. Pat. No. 4,101,457; Pardo, Canadian Pat. No. 290,058; McCarty et al, U.S. Pat. No. 3,627,688; Siebert et al, U.S. Pat. No. 3,574,120 and Fehmerling, U.S. Pat. No. 3,513,071.

Furthermore, nothing in the prior art discloses, suggests or teaches that enzymes chosen from the same or similar, subgroup may become cooperative or synergistic. Also, the art does not disclose or suggest that combining enzymes within the same or related subgroup results in a stable mixture without addition of chemical stabilizers or other modifiers.

Bloching, et al, U.S. Pat. No. 4,122,999 (corresponding to British Patent Specification No. 1, 582, 200) propose a stabilized liquid enzyme cleaning composition having an enzyme preparation containing enzymes selected from proteases, amylases and mixtures thereof, a nonionic surfactant, an anionic surfactant, a monovalent alcohol, and an alkoxylated alkylamine (contended to act as an enzyme stabilizer). In one example (Example 10a in Table I), two similar enzymes are depicted in combination, namely, Maxatase ® and Esperase ®.

In Table II of Bloching, et al, residual activities of the 20 examples are shown at 12 and 16 weeks. Bloching et al claims that for the examples (1-10) which have included in their formulas the alkoxylated alkylamine, substantial increase in stability occurs. However, Bloching, et al, do *not* show or suggest cooperative activity or increased stability for combined proteases in Example 10a. Further, the data disclosed in Table III is insufficient to enable any assessment of whether this isolated example of combined proteases has cooperative activity or stability. Thus, no specific benefit from the combining of these two proteases is shown.

There is thus no suggestion in the prior art of an improved enzyme system in cleaning applications which has enhanced enzymatic activity without addition of activators, chemical stabilizers or other modifiers. In cleaning and other applications, a concrete benefit would be obtained if enzyme activity were increased without increasing enzyme concentration, without changing the physical environment of the enzyme and without chemically changing the enzyme.

DISCLOSURE OF THE INVENTION

This invention provides a cooperative enzyme system which is stable under use conditions and which comprises at least two enzymes having activity for a relatively complex substrate, with at least partial activity over the same pH range, wherein the combined activity of the enzymes are greater than the sum of their individual activities as determined by the formula:

$$\left[ \frac{\text{Actual Activity } (E_1 + E_2) - \text{Expected Activity } (E_1 + E_2)}{\text{Expected Activity } (E_1 + E_2)} \right] \times 100\%$$

wherein $E_1$ and $E_2$ are said enzymes.

No additional chemical modifiers, stabilizers or activators are added to the enzyme system of the present invention to provide the increased activity or unexpected stability observed.

Preferred enzymes herein are proteases having optimal activity in alkaline, neutral, acidic media, and mixtures of the same.

In a further embodiment of this invention, the cooperative enzyme system, which is stable under use conditions, further comprises at least two similar enzymes which have similar specificity, similar optical pH and similar responses to temperature and presence of heavy metals and sequestrants, wherein their combined activity with a relatively complex substrate are greater than the sum of their individual activities as determined by the formula:

$$\left[ \frac{\text{Actual Activity } (E_1 + E_2) - \text{Expected Activity } (E_1 + E_2)}{\text{Expected Activity } (E_1 + E_2)} \right] \times 100\%$$

wherein $E_1$ and $E_2$ are said enzymes.

No additional chemical modifiers, stabilizers or activators are added to the enzyme system of the present invention to provide the increased activity or unexpected stability.

Particularly preferred enzymes in this embodiment of the invention are those which must be selected from proteases having optimal activity in only alkaline, neutral or acidic media. Especially preferred are alkaline proteases selected from the group consisting essentially of Esperase ®, Alcalase ®, Savinase ®, Maxacal ®, and Maxatase ®.

The preferred enzymes of this invention unexpectedly show cooperative or synergistic behavior, i.e., improved activity, when combined, without addition of chemical activators. They further show unexpected stability in use when combined without the addition of chemical stabilizers or other modifiers.

In still another embodiment of this invention is a method of making a simple, improved activity enzyme system which is stable under use conditions comprising combining at least two enzymes having activity towards a relatively complex substrate, with at least partial activity over the same pH range, wherein the combined activity of the enzymes must be greater than the sum of their individual activities as determined by the formula:

$$\left[ \frac{\text{Actual Activity } (E_1 + E_2) - \text{Expected Activity } (E_1 + E_2)}{\text{Expected Activity } (E_1 + E_2)} \right] \times 100\%$$

wherein $E_1$ and $E_2$ are said enzymes.

No additional chemical stabilizers, modifiers or activators are added to the enzyme system of the present invention to provide the increased activity or unexpected stability.

DETAILED DESCRIPTION OF THE INVENTION

Surprisingly, it has been discovered that the preferred enzymes of this invention not only display cooperative behavior by having enhanced activity when two or more similar or related enzymes are used but also have unexpected stability (i.e., no mutual digestion) in use conditions even though the enzymes so used do not co-occur in nature.

The broadest disclosure of this invention is:

A cooperative enzyme system, which is stable under use conditions, and which comprises at least two enzymes having activity towards a relatively complex substrate, with at least partial activity over the same pH range, wherein the combined activities of the enzymes must be greater than the sum of their individual activity as determined by the formula:

$$\left[ \frac{\text{Actual Activity } (E_1 + E_2) - \text{Expected Activity } (E_1 + E_2)}{\text{Expected Activity } (E_1 + E_2)} \right] \times 100\%$$

wherein $E_1$ and $E_2$ are said enzymes.

No additional chemical modifiers, stabilizers or activators are added to the enzyme of the present invention to provide the increased activity or unexpected stability.

The following definitions are applicable to this disclosure:

Similar or related enzymes: Proteases are the preferred enzymes of this invention. Proteases are but a subclass of hydrolases. Proteases themselves are further divided into three distinct subgroups which are based on the members of the subgroups' pH optima (i.e., optimal activity over a certain pH range). These three subgroups are the alkaline, neutral and acidic proteases. Thus, similar enzymes may be exemplified by enzymes selected solely from one subgroup, eg., alkaline proteases. Related enzymes, on the other hand, indicate that at least one enzyme has been chosen from one subgroup, eg., alkaline protease, while at least one other has been chosen from another, eg., neutral protease.

Cooperativity (or Synergism) occurs when the measured, or actual activity of the combined enzymes are shown to be greater than the sum of the individual enzymes. Thus, enhanced, or improved activity of the combined enzymes over the additive sum of the individual enzymes' activities suggest cooperativity or synergism.

Stability of the two or more proteases would be dependent on a number of factors. Enzymes have optimal activity at certain optimal pH's. For example, common digestive enzymes pepsin and rennin present in most mammalian stomachs have greatest activity at acidic pH's (i.e., below pH 7). Papain, on the other hand, is a neutral protease, while Maxacal ® (brand name of Gist-Brocades N.V.) and Esperase ® (brand name of Novo Industri A.B.) are alkaline proteases. Combining, for example, a neutral protease with an acidic protease might affect the rate of reaction depending on what the reaction pH's were. If the reaction is more acidic, the acidic protease will have optimal activity. However, some slight or even noticeable increase in overall activity may be noted because the neutral protease, although not fully active, might contribute an additional, although comparatively slight, hydrolysis of the substrate. It thus would be surprising if combining proteases of differing pH optima (i.e., optimal activity within defined pH range) would result in enhanced activity over that of the sum of the individual enzymes.

Stability in use conditions: As noted above, stability is dependent upon many conditions. But for the purposes of this invention, "stability in use" is used herein to refer to the observed stability which is surprising because it is expected that combining the similar and related enzymes herein would result in instability due to the possibility of cross-digestion (i.e., one enzyme attacking the other, since, for example, one protease may attack another protease as a source of peptide bonds), or mutual digestion (two proteases attack each other). In either case, *lessened* activity would indicate instability in use conditions. In the enzymes of this invention, such cross-digestion or mutual digestion did not occur. Such stability was certainly unexpected.

Non-co-occurrence: Enzymes which are naturally co-occuring, eg., rennin and pepsin, are not included in the composition claims in this invention. The enzymes of this invention have been carefully selected and assayed to see whether their combination would result in enhanced activities.

Relatively complex substrate: Examples of relatively complex substrates would be proteins, or combinations of protein and other compounds (eg., cell membranes, which can be thought of as protein and lipid sandwiches). Protein is made up of many diverse amino acids arranged in certain sequences, and held together with peptide bonds. Carbohydrates and lipids, on the other hand, may not be relatively complex substrates since both include relatively simple polymers whose basic repeating subunit does not alter. While branching may occur in such relatively non-complex substrates, they still are not considered to be relatively complex substrates since specificity of enzymes directed to those substrates appears limited only to hydrolyzing the interior of the polymer (eg., endo-amylase) or the ends (eg., exo-amylase).

At least partial activity over the same pH range: As previously discussed, it appears that if two enzymes, eg., one neutral and one alkaline protease are combined, their differing pH optima suggest that little or no increase in combined activity over their individual activities would be seen. Surprisingly, the invention shows that if the two enzymes have at least some or partial activity over the same pH range, some combinations of enzymes of differing pH optima will show enhanced activity.

As detailed further below in TABLES I and II, particularly effective combinations of enzymes of differing pH optima were Milezyme ®, which was determined to be a neutral protease, and one enzyme selected from the alkaline proteases Esperase ®, Alcalase ®, Savinase ®, Maxacal ®, and Maxatase ®.

$E_1$ and $E_2$ are symbols for the enzymes used herein. Of course, applicant do not limit the number of similar or related enzymes which can be used herein. $E_3$, $E_4$, $E_5$, etc., may also be added, so long as enhanced activity is observed.

Additional chemical modifiers, stabilizers and activators:

In many of the enzymes of this invention, chemical modifiers and stabilizers may have been added by their respective manufacturers to increase and stabilize their "shelf life." In the enzyme systems of this invention, no chemical or other modifiers or stabilizers are added beyond those already present in the manufacturer's formulas.

Additionally, certain enzymes appear to be activated by certain ions, such as calcium. No activators are added in this invention. By the absence of additional chemical modifiers, stabilizers and activators, the present invention presents an improved, yet *simplified* system over the present art.

Specificity refers to the fact that a change around the reactive bond on the substrate may affect the activity of the enzymes for that substrate. For example, in the structure on page 14, line 9, below, the hydrophobicity or hydrophilicity of $R_2$ would be of great importance to the activity of the enzymes at this linkage. Some enzymes may no longer be able to catalyze this linkage, if $R_2$ is changed, for example, (eg., from $-CH_2COO^-$ to $-CH(CH_3) CH_2CH_3$).

The preferred cooperative enzymes are selected from proteases having optimal activity in acidic, neutral or alkaline aqueous media.

Acidic proteases include, but are not limited to rennin and pepsin.

Neutral proteases include, but are not limited to, papain, trypsin, chymotrypsin and carboxypeptidase. Milezyme ® (brand name of Miles Laboratory), has also been determined to contain at least some activity in neutral pH, and hence, is classified as a neutral protease.

Alkaline proteases include:

| ENZYMES | MANUFACTURER |
| --- | --- |
| Enzymes AP densified | Monsanto Company, Missouri, USA |
| Esperase | Novo Industri A/S, Bagsvaerd, Denmark |
| Ficin | Takamine, Clifton, New Jersey (Miles) |
| HT proteolytic enzyme 200 | Miles Laboratories, Inc. Elkhart, Indiana, USA |
| HAT proteplytic enzyme 7XB | Miles Laboratories, Inc. Elkhart, Indiana, USA |
| Matsulase MGI-10+/20 | Matsutanie Chemical & Co. Ltd Japan (Mitsubishi) |
| Maxatase | Gist Brocades NV, Delft, Netherlands |
| Optimase | Miles Kali-Chemie GmbH Nienburg, West Germany |
| P-11 concentrate | Rohm & Haas, Philadelphia, Pennsylvania, USA |
| Pronase | Kaken Chemical Company, Japan |
| Protease 2200 A | Rohm & Haas GmbH, Darmstadt, West Germany |
| Protease AP 10 x | Schweizerische Ferment AG, Basel, Switzerland |
| Protease B-4000 | Sandoz, Basel, Switzerland |
| Protease Hoechst 1549-1 | Farbwerke Hoechst, Frankfurt, West Germany |
| Protin AS | Daiwa Kasei KK, Osaka, Japan |
| Rapidase 75 | Societe Rapidase, Seclin, France |
| Rapidase 400 | Societe Rapidase, Seclin, France |
| Rhozym J-25, PF | Rohm & Haas, Philadelphia, Pennsylvania, USA |
| Sandoz AP | Sandoz, Basel, Switzerland |
| SP 88 | Novo Industri A/S, Bagsvaerd, Denmark |
| Tasinase B-11-100 | Kyowa Hakko Co., Japan |
| Thermoase | Daiwa Kasei KK, Osaka, Japan |
| Wallerstein 627-P | Wallerstein Company, Staten Island, New York, USA |
| Alcalase | Novo Industri A/S, Bagsvaerd, Denmark |
| Alkaline protease | N.V. Organon-Oss-Niederlande, Netherlands |
| Alkaline protease 200+/290 | Takeda Chemical Industries, Japan |
| Bioprase | Nagase & Co., Ltd., Osaka, Japan |
| Bromelain | Takamine, Clifton, New Jersey (Miles) |
| CRD protease (contains some α-amylase) | Monsanto Company, St. Louis Missouri, USA |
| Enzyme AG-22 | Monsanto Company, St. Louis Missouri, USA |

A further very preferred form of this invention is when similar enzymes, i.e., those of the *same* subgroup, are chosen. As examples thereof, at least two enzymes are chosen from only one of the subgroups of alkaline, neutral or acidic proteases.

This can be described as:

A cooperative enzyme system which is stable under use conditions which comprises at least two similar enzymes which must have similar specificity, similar optimal pH and similar responses to temperature and presence of heavy metals and sequestrants, wherein their individual activity towards relatively complex substrates must be greater than the sum of their combined activities as determined by the formula:

$$\left[ \frac{\text{Actual Activity } (E_1 + E_2) - \text{Expected Activity } (E_1 + E_2)}{\text{Expected Activity } (E_1 + E_2)} \right] \times 100\%$$

wherein $E_1$ and $E_2$ are said similar enzymes; and wherein said enzyme system contains no additional chemical modifiers, stabilizers or activators.

Of these, especially preferred are alkaline proteases selected from Esperase ®, Maxatase ®, Alcalase ®, and additionally, Maxacal ® (also known as PB-92 or Maxazyme) (brand name of Gist Brocades N.V.) and Savinase ® (brand name of Novo Industri A/S). These foregoing alkaline proteases, are believed to belong to the group widely known as subtilisins, reflecting their bacterial origin from various strains of *Bacillus subtilis*. These alkaline proteases are also known as serine proteases since they each have a serine residue at their active site, have at least some esterolytic activity, and optimal activity at alkaline pH (ranging from neutral to 11). They are generally neither inhibited by metal chelating reagents (sequestrants) and thiol poisons nor activated by metal ions or reducing agents. They are, however, generally sensitive to organophosphorous reagents such as diiso-propylphosphofluoridate (DFP) and isopropylmethylphosphofluoridate (Sarin), leading to their further general classification as DFP—sensitive proteases. These alkaline proteases all have relatively broad substrate specificities. They generally have molecular weights in the range of 20,000 to 28,000, isoelectric points in the range of pH 9 to 10.5, and are stable in pH from 5-6 to 9-10 at lower temperatures. The amount of enzyme used for each $E_1$ and $E_2$, etc. is dependent upon a number of variables, to wit: price, proportion of enzyme in the manufacturer's formula, individual activity, intended end use, etc. The enzyme pairs, $E_1$ and $E_2$, were adjusted in proportions sufficient to show improved activity when $E_1$ and $E_2$ were combined. Due to differing manufacturers' concentrations, $E_1$ and $E_2$ were adjusted from 1:5 to 5:1.

With particular reference to the alkaline proteases, or subtilisins, it is thought that their surprising cooperativity and unexpected stability result from their similarity. Further, at least one study has shown that two substilisins, at least one of which is believed to be among the preferred enzymes, Alcalase ®, differ from each other in only 84 of 275 amino acid residues in the single peptide chain. This may account for the subtilisins' remarkable similarity of behavior, without being identical. It has been further proposed that this similiarity is the result of an evolutionary process wherein the long peptide chains of the subtilisins evolved from shorter precursor peptides.

Enzymes are proteins of large molecular weight (up to 1,000,000 M.W.). While they catalyze various reactions in living systems, the preferred enzymes considered in this invention are proteases. Proteases (or proteinases) are hydrolases (one of the six classes of enzymes as determined by the International Union of Biochemistry). They hydrolyze the peptide bonds between amino acids comprising the structural units of proteins, as shown below.

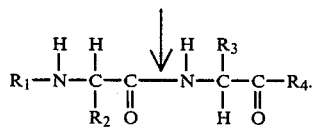

Thus, if the substrate, or matter being hydrolyzed is a simple substrate, such as a single dipeptide (composed of two amino acids with a single peptide bond between them, i.e., $R_1=H$ and $R_4=OH$), any two or more given proteases would compete for the hydrolyzable peptide bond. Since the different proteases would catalyze the hydrolysis of such a simple substrate at different rates, the overall reaction rate would be a composite, or an average of the two reaction rates.

On the other hand, if the substrate is a large protein, which is a relatively complex substrate, using two or more proteases to hydrolyze the protein might lead to the following events and observations: being a large, complex molecule, the substrate protein would likely have many potential sites for protease attack. However, some internal peptide bonds would not be immediately catalyzable, because the substrate protein might be folded, that is have not only a secondary structure, but very probably a tertiary structure, and possibly a quarternary structure. The initial partial hydrolysis would cause some unfolding of the substrate molecule and exposure of some more hydrolyzable bonds. Thus the rate of hydrolysis will be to a great extent determined by the degree of substrate folding and by the locus and rate of the initial hydrolysis reactions in addition to depending on substrate and enzyme concentrations. When two proteases of different specificities are used the reaction of one may aid in unfolding the protein and making an increased number of hydrolyzable sites available to the other. Thus, the reaction rate would depend on which sites on the protein would be attacked, and how rapidly these initial hydrolyses would proceed, thus causing the protein's secondary, tertiary and quaternary structures to unfold, opening up internal peptide bonds to attack.

Temperature and reactivity to heavy metals or sequestrants (i.e., complexing compounds) may also affect the activity of the two or more proteases. For example, papain can be deactivated or "poisoned" by heavy metals such as copper, mercury and zinc, which may bind to critical sites on the protease structure. Other proteases, particularly neutral proteases are deactivated by sequestrants such as tetra-sodium ethylene-diamine-tetra-acetate or 1,10-phenanthroline. Alkaline proteases on the other hand, appear generally less affected by heavy metals or sequestrants.

Also, it is generally accepted that enzyme activity increases with temperatures only to level off rapidly as the enzyme starts to become denatured by certain high temperatures. During denaturation the enzyme molecule begins to unfold losing its most preferred structure and, thereby also, losing its activity.

Further, it should be noted that since proteases are themselves proteins, mixing different proteases together may cause mutual digestion, leading to *lessened* activity.

Lastly, the substrate protein should be considered, as the amount thereof in solution may affect the rate of reaction. For example, the cooperative enzyme pairs will probably not show as dramatic an increase in activity in saturated solution, as in an unsaturated solution. A saturated substrate solution is defined as a solution containing enough substrate protein to tie up all or most of the enzyme in solution. Saturation concentration may further be defined as sufficient substrate protein to bind or tie up about 75.0% of the enzyme in solution.

While it is not entirely understood why these proteases display this unexpected cooperativity and stability, applicants have speculated, although they do not wish to be bound to any one particular theory, that the cooperative behavior of the enzymes results from slight differences in their specificity and will be observed with large, complex substrates.

Slight differences in specificity mean that the preferential hydrolyses of the substrate by each of the enzymes will occur at different points and that the substrate molecule can be simultaneously cleaved by both enzymes. Furthermore, the hydrolysis of the substrate tends to unfold the substrate and expose still more potential sites for hydrolysis causing an apparent rise in substrate concentration and thereby increasing the reaction rate. The advantage in having the two enzymes which are similar or related is that both enzymes can operate near or at their optimal reaction condition. The second advantage of enzyme stability is greatest with proteases which, normally, can digest enzymes since enzymes are proteins themselves.

However, in order to prevent autodigestion proteases are folded so as to hide the vulnerable sites on their surface. The applicants speculate that increased stability with these proteases occurs because proteases with similar specificity may be similarly folded and protected from each other. This would decrease the chance of mutual digestion. This theory is supported by the fact that several subtilisins have been shown to have similar amino acid sequences and, by x-ray crystallography, also similar folding. The practical results of the two enzymes being very similar but not identical, are:

(a) A set of reaction conditions can (but does not have to) be used which are at or near optimal for both enzymes.
(b) The cooperative behavior produces an enhancement of enzymatic activity over and above that obtained at those conditions by individual enzymes.
(c) An unexpected stability over that obtained from using very different enzymes is obtained.

The results of experiments conducted with selected pairs of enzymes appear to bear out the above proposed theory.

In the following section, "ENZYMATIC ASSAYS," two different methods of assaying the preferred enzymes of this invention are disclosed: pH Stat method and TNBS method. While practice has shown TNBS method to be faster and more accurate, in fact, results which are tabulated herein are independent of the means used to find them. Therefore, either TNBS method or pH Stat method can be used to confirm the results obtained in this invention, as well as any other reasonable enzymatic assay.

I. ENZYMATIC ASSAYS

A. pH Stat Method

In this experiment, 15 different pairs of enzymes were assayed by the following method: Each pair of enzymes was introduced into 0.025% Casein solution at about 22.0° C., at pH 9.0 and pH 10.0. Using a Radiometer Autotitrator, activity was monitored and pH was maintained by titrating with 0.1N NaOH solution. The results are expressed in terms of milliequivalents of NaOH per minute × gram.

TABLE I pH STAT METHOD

ACTIVITY VALUES in $\frac{\text{Milliequivalents NaOH}}{\text{minute gram}}$

| | | | | pH = 9.0 | | | | | pH = 10.0 | | | |
|---|---|---|---|---|---|---|---|---|---|---|---|---|
| Example[2] | $E_1$ | | $E_2$ | $E_1$ | $E_2$ | Expected | Actual | Increase | $E_1$ | $E_2$ | Expected | Actual | Increase |
| 1 | Esperase ® | + | Alcalase ® | 2.08 | 4.44 | 6.52 | 6.89 | 0.37 | 2.45 | 4.35 | 6.80 | 6.80 | 0.0 |
| 2 | Esperase ® | + | Savinase ® | 2.08 | 4.98 | 7.06 | 7.69 | 0.63 | 2.45 | 5.06 | 7.51 | 7.89 | 0.38 |
| 3 | Esperase ® | + | Maxacal ®[1] | 2.08 | 2.19 | 4.27 | 4.73 | 0.46 | 2.45 | 3.12 | 5.57 | 6.14 | 0.57 |
| 4 | Esperase ® | + | Maxatase ® | 2.08 | 2.58 | 4.66 | 5.09 | 0.43 | 2.45 | 2.72 | 5.17 | 5.17 | 0.0 |
| 5 | Esperase ® | + | Milezyme ® | 2.08 | 1.35 | 3.43 | 3.43 | 0.0 | 2.45 | 1.22 | 3.67 | 3.88 | 0.21 |
| 6 | Alcalase ® | + | Savinase ® | 4.44 | 4.98 | 9.42 | 10.04 | 0.62 | 4.35 | 5.06 | 9.41 | 9.41 | 0.0 |
| 7 | Alcalase ® | + | Maxacal ®[1] | 4.44 | 2.19 | 6.63 | 6.99 | 0.36 | 4.35 | 3.12 | 7.47 | 7.47 | 0.0 |
| 8 | Alcalase ® | + | Maxatase ® | 4.44 | 2.58 | 7.02 | 7.02 | 0.0 | 4.35 | 2.72 | 7.07 | 7.07 | 0.0 |
| 9 | Alcalase ® | + | Milezyme ® | — | — | — | — | — | 4.35 | 1.22 | 5.57 | 5.57 | 0.0 |
| 10 | Savinase ® | + | Maxacal ®[1] | 4.98 | 2.19 | 7.17 | 8.06 | 0.89 | 5.06 | 3.12 | 8.18 | 8.18 | 0.0 |
| 11 | Savinase ® | + | Maxatase ® | 4.98 | 2.58 | 7.56 | 8.38 | 0.82 | 5.06 | 2.72 | 7.78 | 8.20 | 0.42 |
| 12 | Savinase ® | + | Milezyme ® | — | — | — | — | — | 5.06 | 1.22 | 6.28 | 6.28 | 0.0 |
| 13 | Maxacal ®[1] | + | Maxatase ® | 2.19 | 2.58 | 4.77 | 5.78 | 1.01 | 3.12 | 2.72 | 5.84 | 5.84 | 0.0 |
| 14 | Maxacal ®[1] | + | Milezyme ® | 2.19 | 1.35 | 3.54 | 3.82 | 0.28 | 3.12 | 1.22 | 4.34 | 4.61 | 0.27 |
| 15 | Maxatase ® | + | Milezyme ® | — | — | — | — | — | 2.72 | 1.22 | 3.94 | 3.94 | 0.0 |

[1]Maxacal ® is also known by the brand names "Maxazyme" and "PB-92."
[2]The concentration of enzymes $E_1$ and $E_2$ was adjusted in proportions sufficient to show improved activity when $E_1$ and $E_2$ were combined. Due to differing manufacturer's concentrations, $E_1$ and $E_2$ were adjusted from 1:5 to 5:1.

While increases in activity were observed in nearly all pairs of these selected enzymes at pH 9.0 a more definite method was felt appropriate to show increase in the activity of the paired enzymes. Thus, the increase in activity over that expected was then calculated in percentage according to the formula:

$$\left[ \frac{\text{Actual Activity } (E_1 + E_2) - \text{Expected Activity } (E_1 + E_2)}{\text{Expected Activity } (E_1 + E_2)} \right] \times 100\%$$

and reported below, in TABLE II.

TABLE II

DIFFERENCE FROM EXPECTED ACTIVITY (%)

| | | 0.025% Casein | | | 0.50% Casein | |
|---|---|---|---|---|---|---|
| Example | Enzyme Pair[3] | pH = 9.0 | pH = 10.0 | Example | pH = 9.0 | pH = 10.0 |
| 1 | Esperase ® + Alcalase ® | +5.7 ± 2.2 | +2.6 ± 1.1 | 16 | +4.8 ± 1.0 | −0.5 ± 1.3 |
| 2 | Esperase ® + Savinase ® | +8.9 ± 3.2 | +5.1 ± 0.9 | 17 | +0.6 ± 1.8 | +1.8 ± 2.4 |
| 3 | Esperase ® + Maxacal ®[1] | +10.1 ± 1.6 | +10.1 ± 1.6 | 18 | +3.0 ± 1.4 | +6.1 ± 1.2 |
| 4 | Esperase ® + Maxatase ® | +9.3 ± 2.2 | +0.3 ± 1.7 | 19 | +5.7 ± 0.7 | +0.2 ± 0.8 |
| 5 | Esperase ® + Milezyme ® | +0.2 ± 2.2 | +5.7 ± 0.7 | 20 | +5.0 ± 2.6 | +2.6 ± 1.9 |
| 6 | Alcalase ® + Savinase ® | +6.6 ± 2.7 | +2.9 ± 1.0 | 21 | +0.4 ± 1.7 | +1.8 ± 1.4 |
| 7 | Alcalase ® + Maxacal ®[1] | +5.4 ± 1.4 | +3.7 ± 2.0 | 22 | +2.4 ± 1.5 | — |
| 8 | Alcalase ® + Maxatase ®[2] | +1.3 ± 2.6 | +1.7 ± 1.5 | 23 | +1.2 ± 1.2 | +0.3 ± 1.0 |
| 9 | Alcalase ® + Milezyme ® | — | +1.9 ± 1.2 | 24 | — | +1.4 ± 1.6 |
| 10 | Savinase ® + Maxacal ®[1] | +12.5 ± 2.8 | +3.6 ± 1.6 | 25 | +0.5 ± 2.9 | +2.1 ± 1.2 |
| 11 | Savinase ® + Maxatase ® | +10.8 ± 2.0 | +5.3 ± 1.1 | 26 | +2.9 ± 1.2 | +2.2 ± 0.7 |
| 12 | Savinase ® + Milezyme ® | — | +2.1 ± 1.1 | 27 | — | +2.6 ± 1.7 |
| 13 | Maxaxal ®[1] + Maxatase ® | +21.3 ± 4.0 | +4.4 ± 1.8 | 28 | +1.7 ± 1.5 | +5.6 ± 2.6 |
| 14 | Maxacal ®[1] + Milezyme ® | +8.0 ± 2.4 | +6.3 ± 1.0 | 29 | +3.3 ± 1.8 | +3.7 ± 2.2 |

TABLE II-continued

| | | DIFFERENCE FROM EXPECTED ACTIVITY (%) | | | | |
|---|---|---|---|---|---|---|
| | | 0.025% Casein | | | 0.50% Casein | |
| Example | Enzyme Pair[3] | pH = 9.0 | pH = 10.0 | Example | pH = 9.0 | pH = 10.0 |
| 15 | Maxatase ® + Milezyme ® | — | +3.3 ± 1.5 | 30 | — | +3.8 ± 1.6 |

[1] Maxacal ® is also known by the brand names "Maxazyme" and "PB-92".
[2] Example 8, Alcalase ® and Maxatase ®, did not show any appreciable increase in activity.
[3] The enzyme pairs, $E_1$ and $E_2$, were adjusted in proportions sufficient to show improved activity when $E_1$ and $E_2$ were combined. Due to differing manufacturer's concentrations, $E_1$ and $E_2$ were adjusted from 1:5 to 5:1.

B. TNBS Method

A further method of assaying the activity of the preferred enzymes of this invention involves using the TNBS color reaction method and the Technicon Autoanalyzer. This assay measures the enzymatic hydrolysis of casein into polypeptides containing free amino groups. These amino groups react with 2,4,6-trinitrobenzene sulfonic acid (TNBS) to form a yellow colored complex, as depicted by the following reaction:

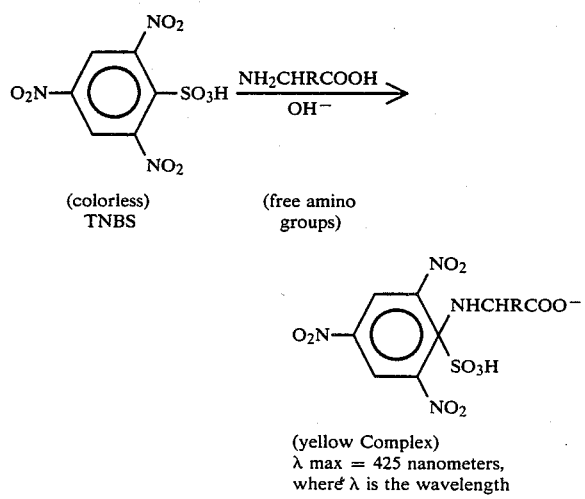

(colorless)    (free amino
TNBS        groups)

(yellow Complex)
λ max = 425 nanometers,
where λ is the wavelength

Thus, the more deeply colored the reaction, the more activity is measured. In practice, this method of assay was found to be faster and more accurate than the pH-stat method, outlined above.

II. DATA MEASUREMENT AND ANALYSIS

All measurements of the chosen enzyme pairs were taken at 52±1° C. and at pH values of 9.0 and 10.0. The enzyme mixtures were sampled immediately after mixing and after sixty minutes at room temperature. Hammersten casein was used as the substrate at 0.50% and 0.025%. These levels represent substrate amounts respectively, saturating and well below saturation.

Direct absorbance readings were used in all calculations. For each enzyme pair, the expected absorbance is the average absorbance of the two separate enzymes. The results are reported as the percent difference between the expected absorbance and the actual absorbance of the combined enzyme pair.

Although in this invention, any increase in combined activity of the two or more enzymes is contended to fall within the broad concept of synergism or cooperation, it was felt that particularly significant increases in activity might be more accurately determined. Thus, standard error analysis was applied to the trials run on each pair of preferred enzymes. This is detailed as follows:

Several trials were run, using TNBS Method, wherein measurements of increased activity were obtained in absorbance/gram units. These were converted to present increase of actual combined activity over expected activity. Error associated with each trial or sampling was pooled. In taking two series of samplings, over a period of two days, the pooled errors were computed as follows:

$$S_p = \sqrt{\frac{S_1(n_1 - 1) + S_2(n_2 - 1)}{n_1 + n_2 - 6}}$$

wherein
$S_p$ = Pooled Standard Deviations, or random errors,
$S_1$ = sum of error in determining absorbance of $E_1$ and $E_2$ (separate enzymes),
$S_2$ = sum of error in taking the mean (averaged) trials for increased activity for $E_1$ and $E_2$,
$N_1$ = number of samples for first series of trials
$N_2$ = number of samples for second series of trials.

In pooling the standard deviations, two assumptions are made.
1. The two means are independent.
2. $\delta_1 = \delta_2$, where $\delta_1$ and $\delta_2$ are the summed errors.

This thus led to the conclusion that the most significant, and therefore, preferred determinations of increased activity can be characterized as:

Increased activity (i.e., actual activity-expected activity × 100%) which is greater than or equal to twice the error in the determination of the activity of the combined enzymes, said error calculated by the foregoing pooled error formula.

Especially preferred values determined in this manner for similar enzymes are shown above in TABLE II, by the circled values in Examples 1–4, 6–7, 10–11, 13–14 at pH 9, and 1–3, 5–6, 10–11 and 13–15 at pH 10, both at 0.025% casein; and 16, 18–19 and 26 at pH 9 and 18, 26, 28 and 30 at pH 10, both at 0.5% casein. Examples 5 (pH 10), 14 (pH 9 and 10), 15 (pH 10) and 30 (pH 10) show that related enzymes, here, Milezyme ® and, respectively, Esperase ®, Maxacal ® or Maxatase ® can combine to produce greatly enhanced activities even though they are not from the same subgroup.

A trial was run in the absence of substrate for each enzyme pair in TABLE II to see if any mutual digestion occured. No increase in color or any color change was observed, indicating no new terminal amines had been produced, thus signifying that mutual digestion had not occured. This shows that the similar or related enzymes of this invention are stable in the presence of each other without chemical stabilizers or other modifiers.

From the foregoing results, it is evident that the cooperative enzymes of this invention can yield substantial benefits in at least two areas:

(1) Cost is a paramount concern of most enzyme uses. By combining suitable combinations of these enzymes, eg., one half of a more expensive enzyme and one half inexpensive enzyme, the same benefit may be realized at lower cost. (2) As greater activity is seen in these combinations, a lesser total amount of combined enzymes may yield as great a benefit as a larger amount of a single enzyme. Secondly, a greater benefit will likely be seen if the same total amount of combined enzymes is used as opposed to same total amount of a single enzyme.

The foregoing examples and assays are in no way intended to limit the scope or manner of intended use of this invention. For example, although cleaning applications (laundry detergents, dry or liquid bleaches, household cleaners, prewashes) have been mentioned as possible uses of the enzymes of this invention, the increased activity enzyme systems of this invention can have numerous applications, whether industrial, commercial, or in purely research directed activities. For example, improved contact lens cleaning compositions may be achieved by using these enzymes. Hard contact lenses, and soft contact lenses are subject to contamination from various protein-type substances, including, but not limited to the lysozyme present in the tears bathing the eyes, dust particles from the surrounding atmosphere, and mucin.

The cooperative enzymes of this invention could also be used for meat tenderizing purposes, as for example, where papain or trypsin have been used. Also, printing equipment utilizing protein-based gums in inks could be cleaned with cleaning compositions containing these cooperative enzymes. Further, where dehairing is required, such as in the meat and poultry industries, these cooperative enzymes could be used to reduce the amount of effort required in what is generally a labor intensive industry.

Since dehairing in the poultry industry is generally accomplished by flashing quick jets of ignited natural gas over the plucked poultry to singe the small pinnules remaining on the poultry, recent efforts to decrease the use of natural gas in this country would be aided thereby. Fish scaling could likely also be accomplished by using compositions of this invention. Further, shellfish could be "shucked" by utilizing various combinations of the improved activity, cooperative enzymes of this invention.

What is claimed is:

1. A stable, cooperative enzyme system comprising at least two enzymes having activity for a relatively complex substrate which must contain at least one protein, with at least partial activity over the same pH range, wherein their combined activity is greater than the sum of their individual activities as determined by the formula:

$$\frac{[\text{Actual Activity } (E_1 + E_2) - \text{Expected Activity } (E_1 + E_2)]}{\text{Expected Activity } (E_1 + E_2)} \times 100\%$$

wherein $E_1$ and $E_2$ are said enzymes;
wherein said enzymes are alkaline or mixtures of alkaline and neutral proteases; and
wherein no stabilizers are present when said enzymes are mixtures of alkaline and neutral proteases.

2. The cooperative enzyme system of claim 1 wherein said enzymes include a first enzyme which is a neutral protease and at least a second enzyme which is an alkaline protease.

3. The cooperative enzyme system of claim 2 wherein said first enzyme is Milezyme ®.

4. The cooperative enzyme system of claim 2 wherein said second enzyme is selected from the group consisting essentially of Esperase ®, Alcalase ®, Savinase ®, Maxacal ®, and Maxatase ®.

5. A stable, cooperative enzyme system comprising at least two similar enzymes having similar specificity, similar optimal pH, wherein their combined activity towards a relatively complex substrate which must contain at least one protein, is greater than the sum of their individual activities as determined by the formula:

$$\frac{[\text{Actual Activity } (E_1 + E_2) - \text{Expected Activity } (E_1 + E_2)]}{\text{Expected Activity } (E_1 + E_2)} \times 100\%$$

wherein $E_1$ and $E_2$ are said similar enzymes;
wherein said enzymes are alkaline or mixtures of alkaline and neutral proteases; and
wherein no stabilizers are present when said enzymes are mixtures of alkaline and neutral proteases.

6. The cooperative enzyme system of claim 5 wherein said enzymes are at least two proteases having optimal activity in alkaline media.

7. The cooperative enzyme systme of claim 6 wherein said enzymes are selected from the group consisting essentially of Esperase ®, Alcalase ®, Savinase ®, Maxacal ®, and Maxatase ®.

8. The cooperative enzyme system of claim 7 wherein said enzymes are Esperase ® and Alcalase ®.

9. The cooperative enzyme system of claim 7 wherein said enzymes are Esperase ® and Savinase ®.

10. The cooperative enzyme system of claim 7 wherein said enzymes are Esperase ® and Maxacal ®.

11. The cooperative enzyme system of claim 7 wherein said enzymes are Esperase ® and Maxatase ®.

12. The cooperative enzyme system of claim 7 wherein said enzymes are Alcalase ® and Maxacal ®.

13. The cooperative enzyme system of claim 7 wherein said enzymes are Alcalase ® and Savinase ®.

14. The cooperative enzyme system of claim 7 wherein said enzymes are Savinase ® and Maxacal ®.

15. The cooperative enzyme system of claim 7 wherein said enzymes are Savinase ® and Maxatase ®.

16. The cooperative enzyme system of claim 7 wherein said enzymes are Maxacal ® and Maxatase ®.

17. A stable, cooperative enzyme system comprising at least two enzymes which are alkaline, or mixtures of alkaline and neutral proteases;
wherein no stabilizers are present when said enzymes are mixtures of alkaline and neutral proteases.

18. The cooperative enzyme system of claim 17 wherein said enzymes include a first enzyme which is a neutral protease and a second enzyme which is an alkaline protease.

19. The cooperative enzyme system of claim 18 wherein said first enzyme is Milezyme ®.

20. The cooperative enzyme system of claim 18 wherein said second enzyme is selected from group consisting essentially of Esperase ®, Alcalase ®, Savinase ®, Maxacal ®, and Maxatase ®.

21. The cooperative enzyme system of claim 17 wherein said enzymes are alkaline proteases.

22. The cooperative enzyme system of claim 21 wherein said enzymes are selected from the group consisting essentially of Esperase ®, Alcalase ®, Savinase ®, Maxacal ®, and Maxatase ®.

23. The cooperative enzyme system of claim 22 wherein said enzymes are Esperase ® and Alcalase ®.

24. The cooperative enzyme system of claim 22 wherein said enzymes are Esperase ® and Maxatase ®.

25. The cooperative enzyme system of claim 22 wherein said enzymes are Alcalase ® and Maxacal ®.

26. The cooperative enzyme system of claim 22 wherein said enzymes are Alcalase ® and Savinase ®.

27. The cooperative enzyme system of claim 22 wherein said enzymes are Savinase ® and Maxacal ®.

28. The cooperative enzyme system of claim 22 wherein said enzymes are Savinase ® and Maxatase ®.

29. The cooperative enzyme system of claim 22 wherein said enzymes are Esperase ® and Savinase ®.

30. The cooperative enzyme system of claim 22 wherein said enzymes are Esperase ® and Maxacal ®.

31. The cooperative enzyme system of claim 22 wherein said enzymes are Maxacal ® and Maxatase ®.

32. A method of making a stable, cooperative enzyme system comprising combining at least two enzymes having activity towards a relatively complex substrate, which must contain at least one protein, with at least partial activity over the same pH range, wherein the combined activity of the enzymes is greater than the sum of their individual activities as determined by the formula:

$$\frac{[\text{Actual Activity } (E_1 + E_2) - \text{Expected Activity } (E_1 + E_2)]}{\text{Expected Activity } (E_1 + E_2)} \times 100\%$$

wherein $E_1$ and $E_2$ are said enzymes;

wherein said enzymes are alkaline or mixtures of alkaline and neutral proteases; and wherein no stabilizers are present when said enzymes are mixtures of alkaline and neutral proteases.

33. A method of making a stable, cooperative enzyme system comprising combining at least two similar enzymes, which have similar specificity, similar optimal pH, and wherein their combined activity towards a relatively complex substrate which must contain at least one protein, must be greater than the sum of their individual activities as determined by the formula:

$$\frac{[\text{Actual Activity } (E_1 + E_2) - \text{Expected Activity } (E_1 + E_2)]}{\text{Expected Activity } (E_1 + E_2)} \times 100\%$$

wherein $E_1$ and $E_2$ are said similar enzymes;

wherein said enzymes are alkaline or mixtures of alkaline and neutral proteases; and wherein no stabilizers are present when said enzymes are mixtures of alkaline and neutral proteases.

* * * * *